United States Patent [19]

Ring, Sr.

[11] Patent Number: 5,031,606

[45] Date of Patent: Jul. 16, 1991

[54] BRACE AND HINGE APPARATUS AND METHOD

[75] Inventor: Gregg Ring, Sr., Houston, Tex.

[73] Assignee: Randolph Austin Company, Manchaca, Tex.

[21] Appl. No.: 642,663

[22] Filed: Jan. 17, 1991

[51] Int. Cl.$^5$ ............................ A61F 5/10; A61F 5/00
[52] U.S. Cl. ................................... 128/77; 128/80 C; 128/80 H; 128/80 F
[58] Field of Search ..................... 128/77, 80 R, 80 C, 128/80 H, 80 F, 88

[56] References Cited

U.S. PATENT DOCUMENTS

| | | | |
|---|---|---|---|
| 4,353,361 | 10/1981 | Foster | 128/80 C |
| 4,502,472 | 3/1985 | Pansiera | 128/80 F |
| 4,520,802 | 6/1985 | Mercer et al. | 128/80 F |
| 4,520,804 | 6/1985 | Digeorge | 128/80 C |
| 4,655,201 | 4/1987 | Pirmantgen | 128/80 C |
| 4,681,097 | 7/1987 | Pansiera | 128/80 C |
| 4,732,143 | 3/1988 | Kausek et al. | 128/80 C |
| 4,817,588 | 4/1989 | Bledsoe | 128/80 C |
| 4,928,676 | 5/1990 | Pansiera | 128/80 C |
| 5,000,169 | 3/1991 | Swicegood et al. | 128/80 C |
| 5,002,044 | 3/1991 | Carter | 128/77 |

Primary Examiner—Richard J. Apley
Assistant Examiner—Lynne Reichard
Attorney, Agent, or Firm—J. Nevin Shaffer, Jr.; Russell D. Culbertson

[57] ABSTRACT

A brace and hinge apparatus having upper and lower brace members and a hinge, with a female half and a male half, attached to these upper and lower brace members. The female half contains an inner bearing surface and the male half contains a locking device for locking dowels against the inner bearing surface of the female half and, thereby, the brace members in one, locked, direction and allowing unlimited movement in another, free, direction. A lock release is provided for allowing movement in the locked direction when desired. Further, a tensioner is provided for providing constant tension to the upper and lower brace members in the free moving direction thereby providing constant therapeutic affect when in use. Additionally, a brake is provided to lock the device against movement in the free direction and to relieve the tension from the tensioner when so desired. Additionally, a stop device is included to prevent hyperextension of a joint to which the brace and hinge is attached by preventing movement beyond a certain degree.

21 Claims, 5 Drawing Sheets

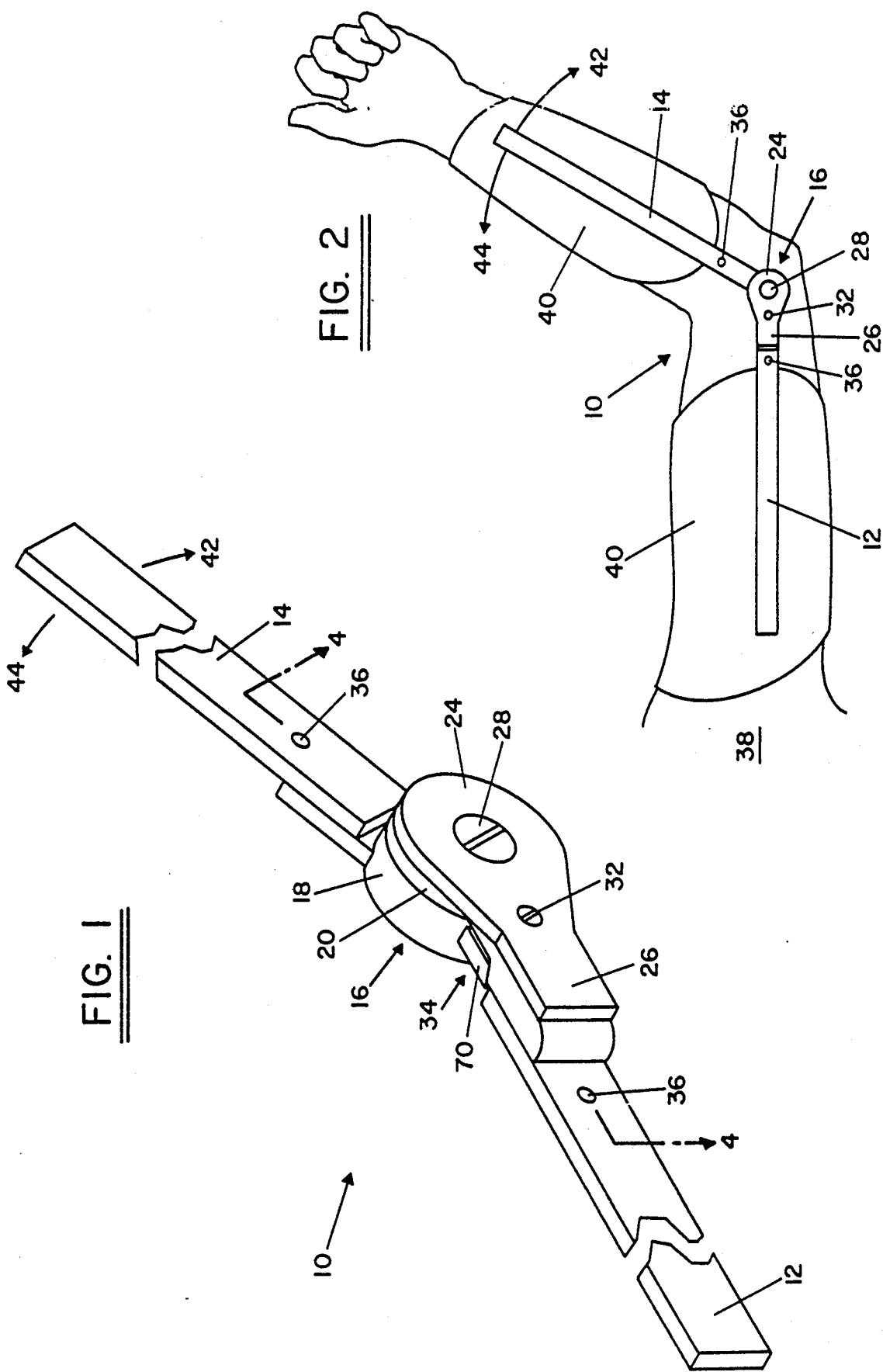

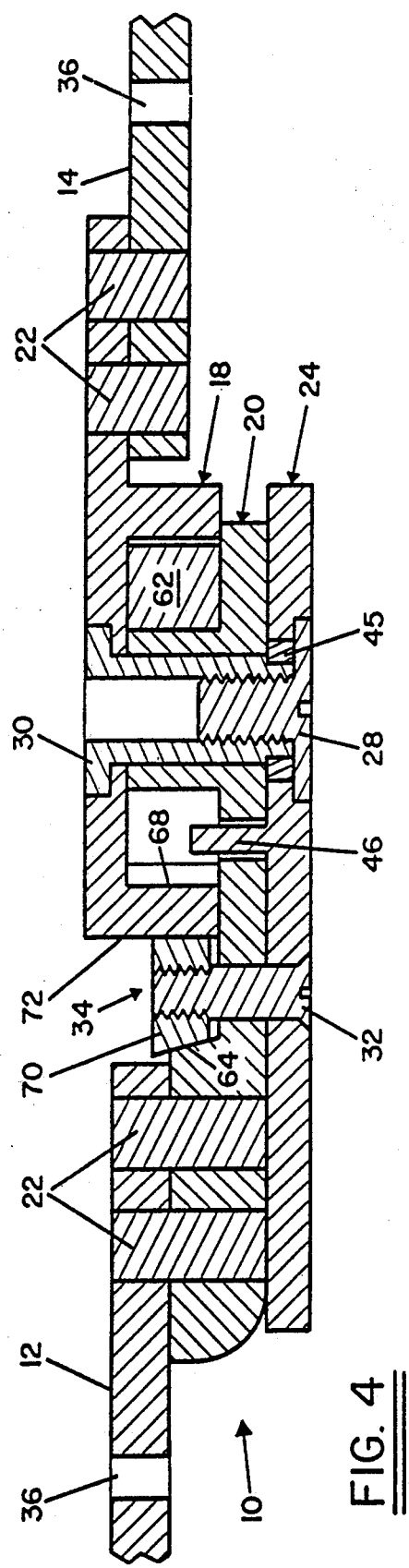
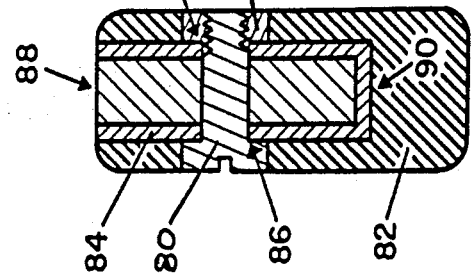
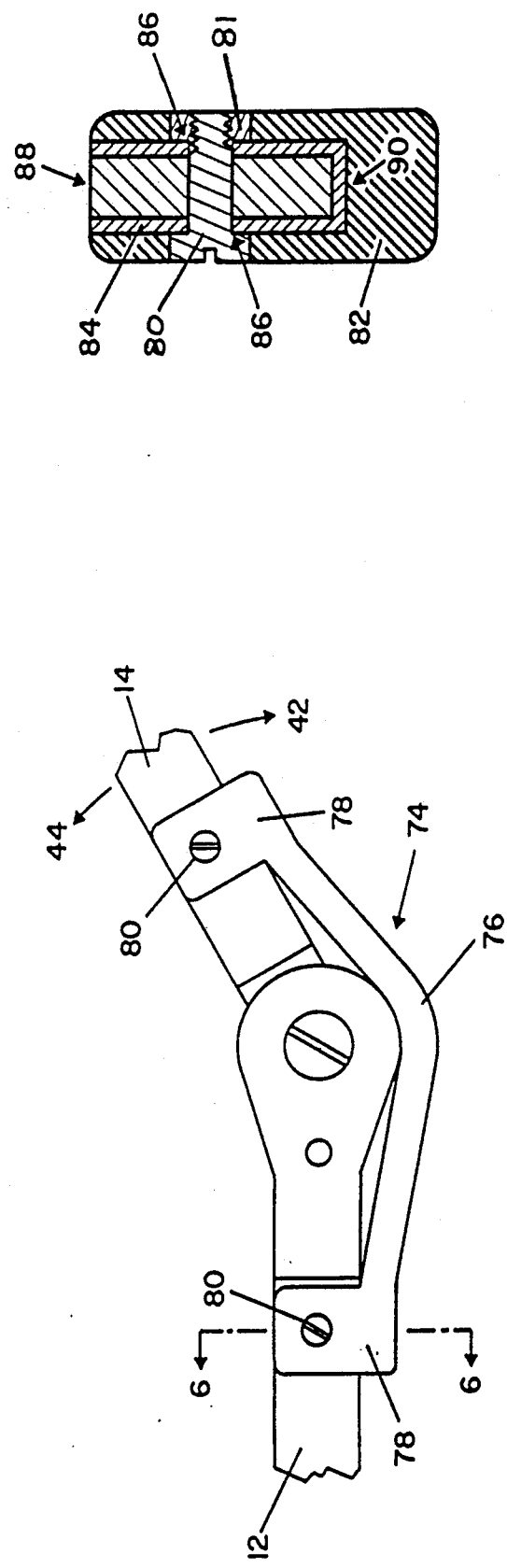

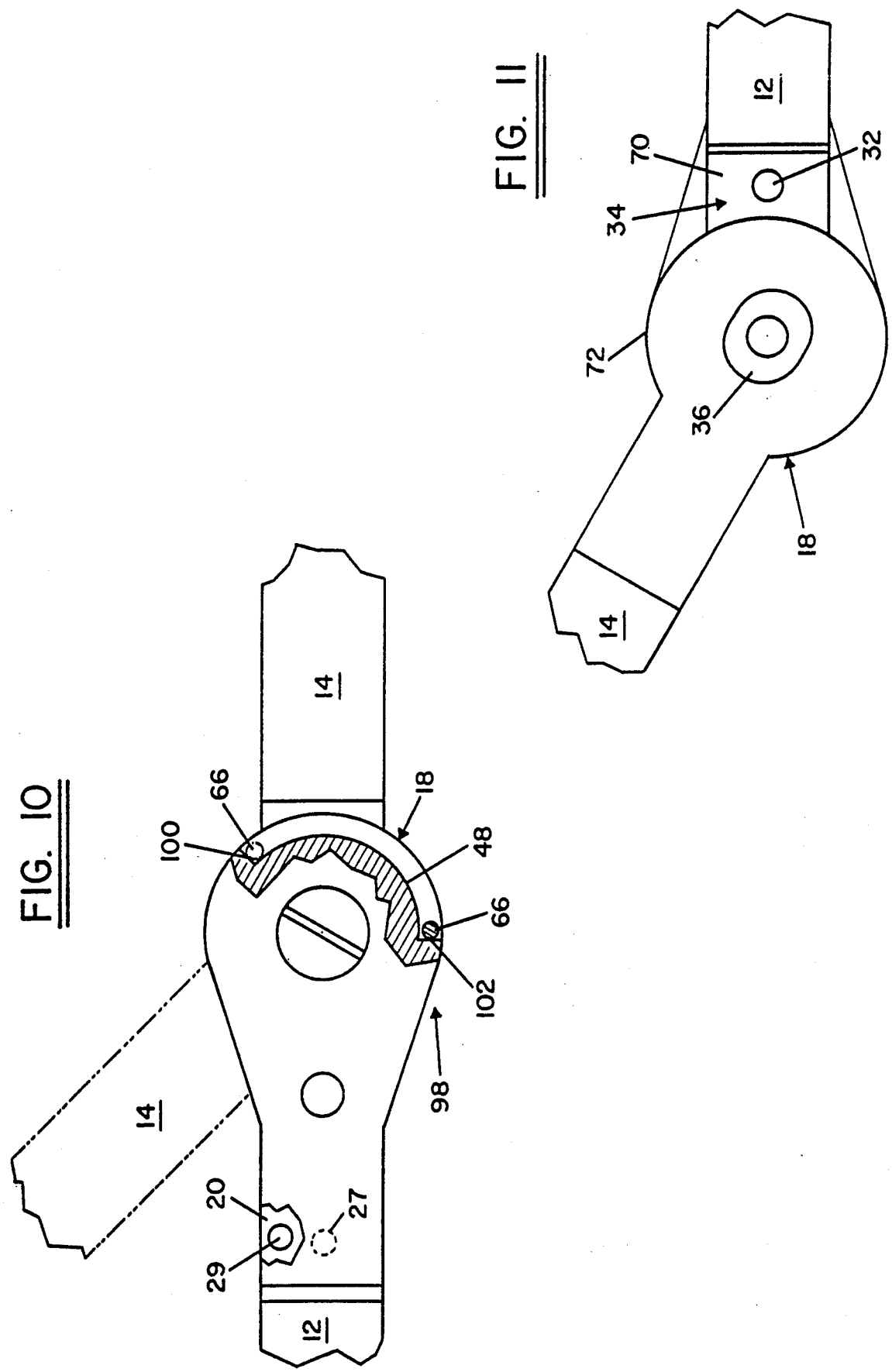

BRACE AND HINGE APPARATUS AND METHOD

BACKGROUND OF THE INVENTION

This invention relates to an improved brace and hinge apparatus and method for maintaining advances obtained through therapy and the like. In particular the device relates to hinges and braces for use in orthopedic appliances.

A wide variety of braces and hinges for use in orthopedic appliances have been known in the art for quite some time. For example, most hinge and brace devices in the art are directed to orthotic devices with some manner of locking hinges. Some are adapted to provide pivoting between brace members only in a certain range of movement. An example of such a limited range of movement device is disclosed in Bledsoe, U.S. Pat. No. 4,817,588, which utilizes a hinge mechanism which has a single adjustment dial that cooperates with a pair of stop members to selectively limit the relative pivotal movement between the thigh and calf support members associated with the hinge. A restraining strap is used to inhibit extension of the leg beyond the hinge established extension limit angle of the brace. Another such example of a limited range of motion hinge is Kausek et al., U.S. Pat. No 4,732,143, which uses spaced-apart pivotal connections with intermeshing gear teeth. Brace and hinge devices are also known in the art that are adapted to lock in one direction but allow free movement in the opposite direction. DiGeorge, U.S. Pat. No. 4,520,804, uses a ratchet wheel and a pair of rotatable pawls which are selectively manually operable by a user to effectively control the direction of rotation of the ratchet wheel, as well as to lock the ratchet wheel and the brace against further rotation or relative pivotal movement. Pansiera, U.S. Pat. No. 4,502,472, is another example of a hinge that locks in one direction and is free to move in another direction. The hinge in that device includes a rotatable, substantially circular, double-tooth pawl which is slidably encased in a cylindrical housing. There is also provided a ratchet with a plurality of teeth and a means for selectively engaging the pawl in the ratchet for extension only use or not.

A drawback to the brace and hinge devices known in the art is that they are limited in their adjustability by the size of the teeth in the ratchets that are used. That is, they are not infinitely adjustable because of the space the teeth must take up in order to provide a discreet locking position for the hinge. A further drawback is that there is no provision in the prior art for a means for providing a continuous therapy action through the brace. Thus, there is a need in the art for providing a brace and hinge device which is infinitely adjustable and which provides for continuing therapy as desired. It, therefore, is an object of this invention to provide an improved brace and hinge apparatus and method, such as for orthopedic appliances, for infinite incremental adjustment of the hinge and for providing continuous therapeutic action when desired, among other things.

SHORT STATEMENT OF THE INVENTION

Accordingly, the brace and hinge of the present invention includes upper and lower brace members and a hinge, with a female half and a male half, attached to the upper and lower brace members. The female half contains an inner bearing surface and the male half contains a locking device for locking dowels against the inner bearing surface and, thereby, the brace members, in one, locked, direction and allowing unlimited movement in another, free, direction. Further, the invention includes a lock release for allowing movement in the locked direction. Also, a tensioner is provided, for providing constant tension to move the upper and lower brace members in the free moving direction or to resist movement in the free direction. Also, a brake is provided for braking and preventing movement in the free direction and a stop device is provided to prevent hyperextension of a joint to which the brace and hinge is attached.

The infinite adjustability of the device is provided by means of the female half which is comprised of an outer surface, an inner bearing surface within which the locking device and the dowels fit, and a stop peg. The male half comprises an outer race with beginning and ending stops along which the stop peg is free to move from stop to stop. Further, lock release access slots are provided in the male half for actuation of the lock release. Importantly, the locking device formed in the male half of the hinge has at least one dowel receiving slot within which the dowel fits without contacting the inner bearing surface. The locking device further has a gradually narrowing limit within which the dowel is free to move until contacting the inner bearing surface and the sidewall of the limit. The dowel is constantly biased into the position of contacting the inner bearing surface and limit by springs in the locking device. The springs force the dowel into the gradually narrowing limit so that the dowel is constantly, again, in contact with the inner bearing surface and limit. As a result, the hinge instantly locks in the locked direction when any movement in that direction is attempted. On the other hand, when motion in the free direction is attempted the device moves freely. The device is stopped in its free motion by means of the stop peg so that hyperextension of the joint does not occur.

BRIEF DESCRIPTION OF THE DRAWINGS

Other objects, advantages, and features of the present invention will become more fully apparent from the following detailed description of the preferred embodiment, the appended claims and the accompanying drawings in which:

FIG. 1 is a plan view of a preferred embodiment of the brace and hinge of the present invention;

FIG. 2 is a representational view of the brace and hinge shown attached to a user's forearm and upper arm with the hinge at the joint;

FIG. 4 is a sectional view of the invention taken along lines 4—4 of FIG. 1;

FIG. 5 is a top view of the invention of the device with the constant therapeutic tensioner attached;

FIG. 6 is a sectional view of one of the reinforced ends of the tensioning device taken along lines 6—6 of FIG. 5;

FIG. 10 is a top partially cut away view illustrating the operation of the stop of the invention; and FIG. 11 is a bottom view illustrating the brake of the invention.

DETAILED DESCRIPTION OF THE PREFERRED EMBODIMENT

Figure 3:
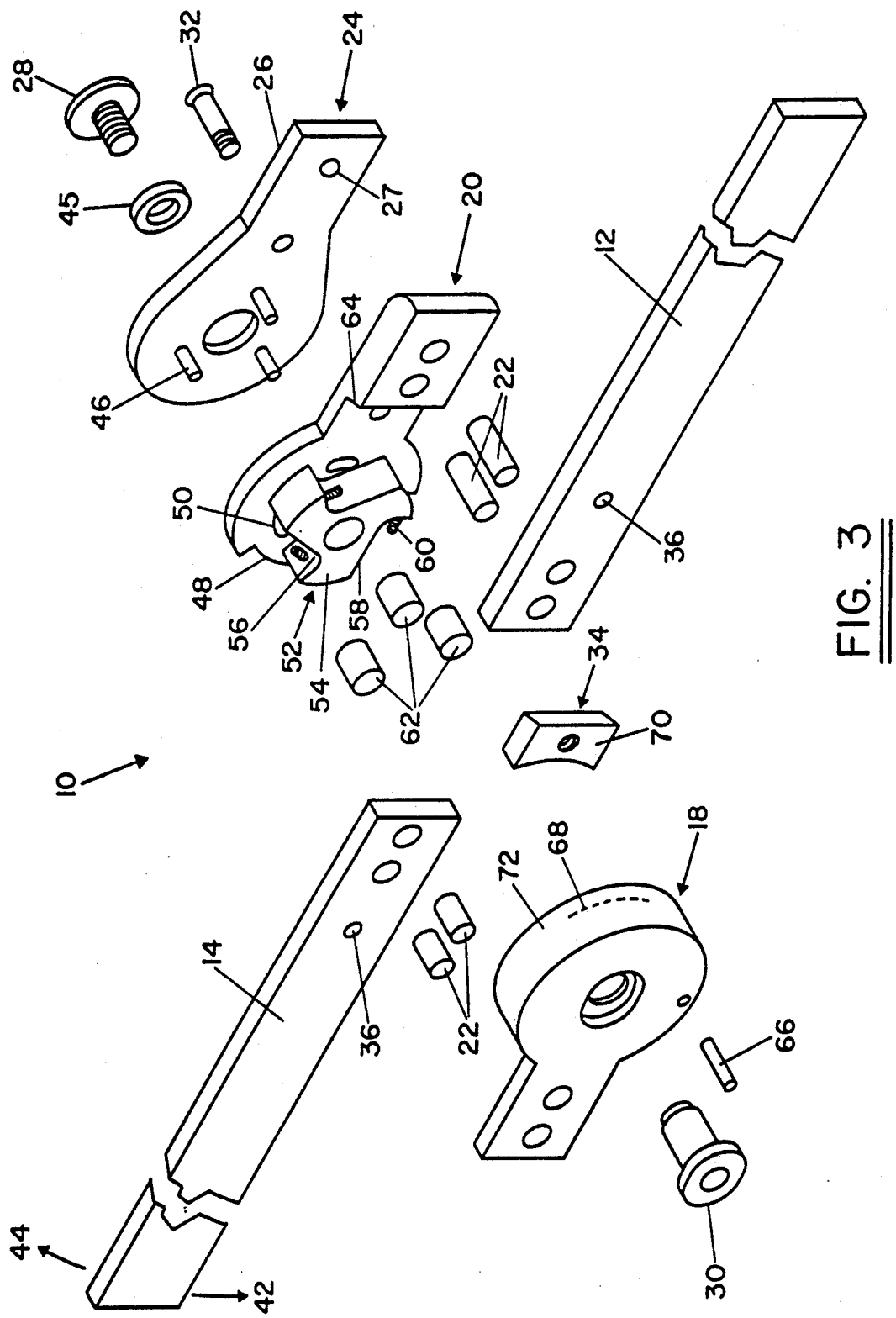
FIG. 3 is an exploded view of the invention of FIG. 1.

The preferred embodiment of the present invention is illustrated by way of example in FIGS. 1–11. With specific reference to FIGS. 1, 2 and 3, a brace and hinge 10 includes upper brace member 12 and lower brace member 14. Hinge 16 has female half 18 and male half 20. Female half 18 is connected to lower brace member 14 by means of rivets 22, welding, or the like and male half 20 is connected to upper brace member 12 in a similar fashion. Attached to male half 20 is lock release 24 with operating extension 26. Operating extension 26 has lock ball 27 that works in conjunction with lock detent 29 so that the brace and hinge 10 may be kept in a free moving position without constant application of pressure on operating extension 26. Lock release 24 is connected to male half 20, and male half 20 is connected to female half 18, by means of hinge screw 28 shoulder nut 30 and spacer ring 45. Also shown is brake screw 32 and brake 34. Also shown are tensioner retaining holes 36 in upper and lower brace members 12 and 14.

FIG. 2 shows the injured left arm of user 38 with brace and hinge 10 attached by means of arm attachments 40, known in the art. Arrow 42 shows the direction of "free" movement of brace and hinge 10 and arrow 44 shows the "locked" direction. In the case where user's 38 left elbow is injured, therapy would be required to regain the ability to fully extend the arm. By means of use of brace and hinge 10 the progress gained in therapy for the extension of the arm, as illustrated in FIG. 2, would be maintained by prohibiting the arm from moving in locked direction 44 but additional therapy would be possible by enabling user's arm 38 to move in the free direction 42.

Referring now specifically to FIG. 3, the exploded view of brace and hinge 10 is illustrated. It shows spacer 45 for hinge screw 28. Lock release 24 is shown with dowel movement pegs 46 attached by any means known in the art such as soldering, welding, and the like. Male half 20 is shown with outer race 48, lock release access slots 50 and lock 52. Lock 52 is comprised of several lock arms 54 which are designed to have a generally larger dowel receiving slot 56 and a gradually narrowing limit 58. Further, lock 52 has lock springs 60 which apply constant pressure on dowels 62. Also, male half 20 has slanted brake face 64 and female half 18 has stop peg 66 and an inner race 68 within which dowel 62 and lock 52 fit.

Referring now to FIG. 4, a section view of brace and hinge 10 is shown taken along lines 4—4 in FIG. 1. Among other things, FIG. 4 illustrates the functioning of brake 34. Brake 34 utilizing brake screw 32 draws lock nut 70 down slanted brake face 64 in the direction of lock release 24. Slanted brake face 64 forces lock nut 70 tightly against outer surface 72 of female half 18 thereby preventing movement of female half 18 in relation to male half 20. Loosening of brake screw 32 allows lock nut 70 to retreat along slanted brake face 64 thereby braking frictional contact with outer surface 72 and allowing hinge 10 to move.

Referring now to FIGS. 5 and 6, tensioner 74 is illustrated. Tensioner 74 is comprised of center tension section 76 and reinforced attachment ends 78. Tensioner 74 is removably attachable to brace and hinge 10 by means of screws 80, bolts, pins or the like. With one end 78 attached to lower brace 14 and one end 78 attached to upper brace 12 tensioner 74 provides therapeutic tension to move user's 38 arm in the free moving direction 42. When user's 38 arm is strong enough, tensioner 74 may be placed on the opposite side of hinge 10 so that movement in the free direction will be resisted and require more strength. By means of tensioner 74, then, constant therapeutic benefits may be obtained through utilization of brace and hinge 10.

FIG. 6 is a section view of reinforced attachment end 78 taken along lines 6—6 of FIG. 5. Reinforced attachment end 78 is comprised of outer flexible material cover 82 and inner hardened material 84. Outer flexible material 82 may be plastic, rubber, or the like or any stretchable material that may provide appropriate tension. Inner hardened material 84 may be made of metal, plastic, or the like. The purpose of inner hardened material 84 is to enable screw 80 and nut 81 to attach reinforced attachment end 78 to brace and hinge 10 securely through recessed screw holes 86 while at the same time preventing stretching at screw holes 86. By means of reinforced attachment end 78, then, stretching and tensioning along tensioner 74 occurs between reinforced attachment ends 78 and center tension section 76 only. FIG. 6 also demonstrates that, in this embodiment, reinforced attachment end 78 forms a "U" shape so that it may slip over the narrow edge of upper and lower brace members 12 and 14. FIG. 6 illustrates this by means of open end 88 and closed end 90.

Figure 7:
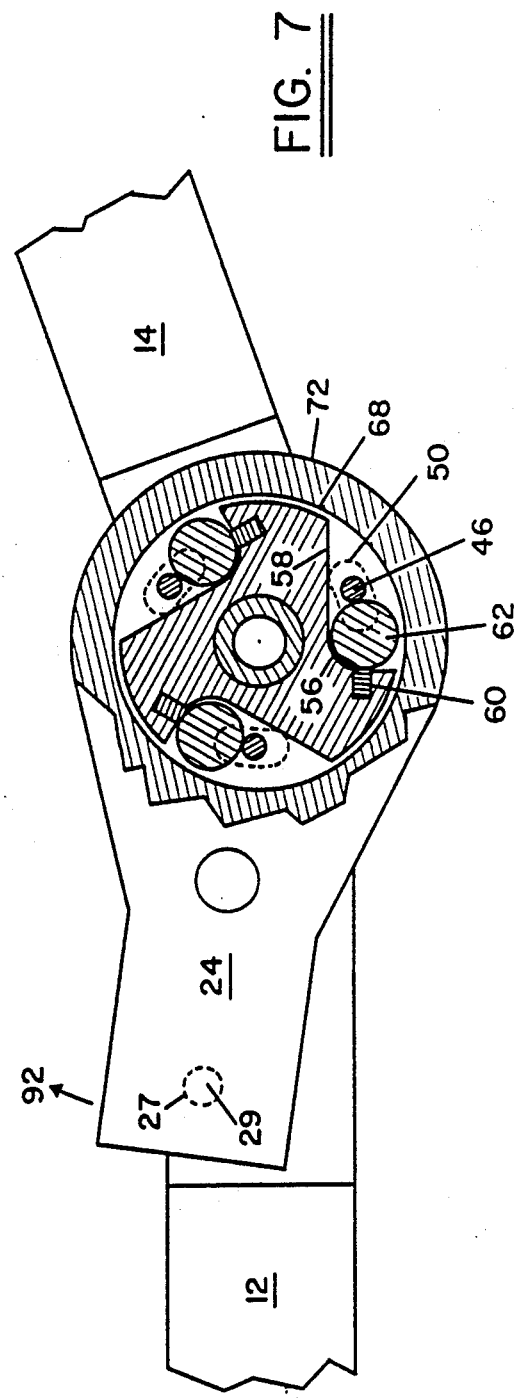
FIG. 7 is a top partially cut away view showing the lock release peg forcing the dowel into the dowel receiving slot and out of contact with the inner bearing surface so that movement in the locked direction is allowed.
Figure 9:
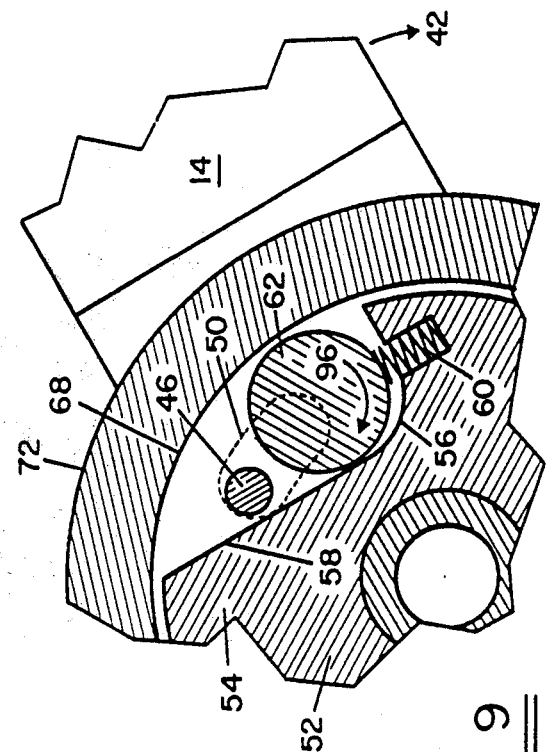
FIG. 9 is a top partially cut away view of the invention of FIG. 1 showing the dowel in the released position so that the hinge may move in the free direction.
Figure 8:
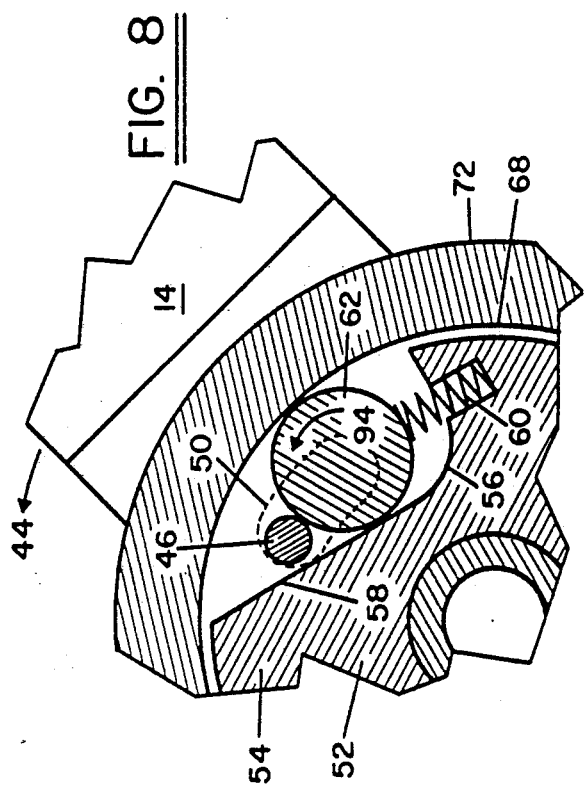
FIG. 8 is a partial top sectional view of the invention showing the dowel in contact with the inner race in the locked position.

Referring now to FIGS. 7, 8 and 9, the operation of lock release 24 and the locked and free moving positions is illustrated. FIG. 7 demonstrates the use of lock release 24 thereby enabling brace and hinge 10 to move freely in either direction. User 38 simply pushes lock release 24 in the direction of arrow 92 thereby moving dowels 62 with dowel movement pegs 46 into dowel receiving slots 56 and compressing lock springs 60. As a result, dowels 62 are no longer in contact with inner race 68 and free movement is permitted in any direction. Ball 27 and detent 29, when engaged, hold lock release 24 in the open position when and if desired.

Referring now to FIGS. 8 and 9, FIG. 8 shows the device of brace and hinge 10 in its normal, resting, locked position 44. In this position, lock springs 60 force dowels 62 out of dowel receiving slots 56 and along gradually narrowing limits 58 of lock arms 54 so that dowels 62 are in contact with inner race 62, dowel movement pegs 46 and the sidewalls of gradually narrowing limits 58 of lock arm 54. In this position any movement in the locked direction 44, attempts to force dowels 62 in the direction of arrow 94 and into an ever increasingly narrow limit. Because the dowel 62 is made of highly incompressible material and/or metal, such as steel, titanium, etc., and because inner race 68 and dowel movement pegs 46 are made of the same material, movement in the locked direction is instantly and constantly prevented.

Referring now to FIG. 9, an illustration of the ability of the device to rotate in free direction 42 at any time is shown. Movement away from the locked direction 44 in the free direction 42 causes dowel 62 to rotate in the direction of arrow 96. This can occur because it is resisted only by lock spring 60 which will compress ever so slightly so that contact with inner race 68 is lost or at least permitted to slide since dowel 62 is moving in the direction of dowel receiving slot 56 which is larger than dowel 62 and thereby insuring that movement will be allowed and not prohibited. Once movement in free direction 42 is stopped lock spring 60 forces dowel 62 against inner race 68 and gradually narrowing limit 58 and dowel movement pegs 46. As a result, referring now to FIG. 8 again, once at rest, any movement in the locked direction 44 will instantaneously lock brace and hinge 10.

A major advantage of the preferred embodiment of this invention is that because there are not ratchet teeth or individual teeth sections to deal with, should a brace as shown in FIG. 2 be desired on both sides of the user's extremity, the intricate coordination required for locking of both devices at the same time, as rarely occurred with devices in the prior art, is easily accommodated. That is, because brace and hinge 10 locks instantly in any position when moving in locked direction 44 a pair of brace and hinges 10 would also work instantaneously and there would never be the case, as often occurs in the prior art, where one side of the brace locked and the other side did not.

Referring now to FIG. 10, a stop device 98 for preventing hyperextension of a joint to which the brace and hinge 10 is attached is illustrated. Stop device 98 is comprised of outer race 48 in male half 20 in combination with stop peg 66 in female half 18. Stop peg 66, and thereby lower brace member 14, is free to move from stop 100 to stop 102 at the beginning and end of outer race 48. Between those stops free movement of lower brace member 14 is permitted.

Referring now to FIG. 11, brake 34 is shown in the full brake position drawn down slanted brake face 64 and into contact with outer surface 72 of female half 18. Brake 34 is used in a variety of situations when movement is no longer desired. For example, should tensioner 74 be attached and constant therapy is no longer desired, brake 34 can be set thereby removing tension from the inured appendage. As shown in FIG. 11, brake screw 32 may be inserted from the side opposite to that shown in FIG. 3 as long as the hole in locked release 24, for brake lock 32, is drilled to receive a screw. In this embodiment, then, access to the brake is provided no matter which side of the user's arm it is attached.

Within the range provided for by the stop device 98, stops 100 and 102 and stop peg 66, an infinitely adjustable therapeutic brace and hinge 10 is provided. Simple and economical in design and manufacturing, brace and hinge 10 is comprised of upper brace member 12 and lower brace member 14 for attachment to user 38. Brace and hinge 10 can be utilized for any of a variety of injuries. In particular elbows, knees, ankles and the like. Additionally, because of the compact simple design of the device, it may also be used for small joints such as fingers which have previously been lacking a suitable brace and hinge such as disclosed herein.

In operation, brace and hinge 10 provide for unlimited movement in one direction, within the limits of stop device 98, but locks instantaneously in the other direction. The primary purpose of this brace and hinge 10 is to prevent loss of range of motion gained during therapy to an injured joint by the injured member constricting after therapy. That is, referring to FIG. 2, after therapy, with brace and hinge 10 in place, user's 38 arm is prevented from moving in the locked direction 44 but is allowed unlimited motion in the free direction 42. As a result, any additional gain in motion made by user 38 would not be lost even after therapy. A combination of devices on the brace and hinge 10 enable it to be used in a variety of additional circumstances. That is, lock ball 27 and lock detent 29 can be used in combination to keep lock release 24 in the open position so that user 38 may move his arm in either direction unrestricted by brace and hinge 10. Further, brake 34 with lock nut 70 and brake screw 32 in combination with slanted brake face 64 can be utilized to lock brace and hinge 10 in any desired position. Additionally, when brace and hinge 10 is used in combination with tensioner 74, constant therapeutic tension is provided to brace and hinge 10 to constantly straighten, or resist straightening, user's arm 38. Obviously, by judicious use of brake 34, tensioner 74 may be left in place while still removing the strain of tension from the user's 38 arm.

An additional, opposite, use of brace and hinge 10 may be anticipated for use with patients that are bedridden for significant periods of time. For patients that are bedridden, it is a natural effect that the foot drops or straightens out as muscles and tendons contract through inactivity. In this case, brace and hinge 10 may be applied to the foot so that motion in the toe up towards the shin direction is permitted while movement of the toe towards the heel, or a flattening of the foot, is prevented.

A primary advantage of the preferred embodiment of this invention is the fact that it is constantly locked in one direction whenever it is at the rest position. Referring to FIG. 8, once again, in the resting position, without interference from lock release 24, brake 34 or stop device 98, brace and hinge 10 will not move in locked direction 44. This is because lock spring 60 forces dowel 62 into gradually narrowing limit 58 of lock arm 54 and into contact thereby with inner race 68, the side of lock arm 54, and dowel movement pegs 46. In this position any movement in locked direction 44 attempts to drive dowel 62 into a space narrower than the diameter of dowel 62. The direction of rotation of dowel 62 is in the direction of arrow 94. Because dowel 62, inner race 68 and lock arms 54 are made of the same hardness of material, dowel 62 may not be compressed and movement is prevented. Conversely, any movement in the free direction 42 is permitted. This is because dowel 96 is being urged in the direction of dowel receiving slot 56 which is larger in diameter than dowel 62. Further, this is because dowel 62 is rotated in the direction of arrow 96 against only lock spring 60. This lock spring will give and, as a result, dowel 62 is free to move away from inner race 68. Dowel 62 does not need to move completely away from inner race 62 in order for a brace and hinge 10 to move in free direction 42. That is, dowel 62 is free to simply slide along the inner race 68 as in fact occasionally happens. Once movement in the free direction stops, however, lock spring 60 forces dowel 62 into the position shown in FIG. 8 where any movement in the locked direction 44 is instantaneously prevented.

A most important advantage of brace and hinge 10 over the prior art is that when brace and hinge 10 is used in a pair, one on each side of the injured member, for example, they will independently function exactly as just described. That is, they will lock instantaneously in the locked direction 44 and will allow unlimited free movement in the free direction 42. Prior art inventions depending on ratchet and teeth combinations very often are unable to be synchronized so that one hinge will exactly move with the other hinge. As a result, one side might lock but the other one would not since it was in between teeth or ratchets. Thus, prior art devices introduced instability to the injured part of the body as opposed to providing support and rigidity as desired.

While the brace and hinge device of the present invention has been disclosed in connection with use with elbows, as shown in FIG. 2, it should be appreciated that the brace and hinge can be used in other situations. In particular, because of its simple design it is particularly useful with small appendages such as fingers, etc. where no previous brace and hinge device was available. The present invention provides an improved brace and hinge which is provided with a unique therapeutic spring tensioning tensioner for constant therapy while in the brace.

While the present invention has been disclosed in connection with the preferred embodiment thereof, it should be understood that there may be other embodiments which fall within the spirit and scope of the invention as defined by the following claims.

I claim:

1. A brace and hinge apparatus comprising:
   (a) upper and lower brace members;
   (b) a hinge means comprising a female half attached to the lower brace member or the upper brace member, a male half attached to the opposite brace member, and a dowel means;
   (c) said female half containing an inner bearing surface;
   (d) said male half containing a locking means for locking said dowel means against said inner bearing surface and, thereby, said brace members, in one, locked, direction and allowing unlimited movement in another, free, direction.

2. The apparatus of claim 1 further comprising a lock release means for allowing movement in said locked direction.

3. The apparatus of claim 1 further comprising a tensioning means for providing constant tension to move said upper and lower brace members in the free-moving direction.

4. The apparatus of claim 1 further comprising a brake means for braking and preventing movement in said free direction.

5. The apparatus of claim 1 further comprising a stop means to prevent hyperextension of a joint to which said brace and hinge is attached.

6. The apparatus of claim 1 wherein said female half further comprises:
   (a) an outer surface;
   (b) said inner bearing surface within which said locking means and said dowel means fit; and
   (c) a stop peg.

7. The apparatus of claim 6 wherein said male half further comprises:
   (a) an outer race with beginning and ending stops along which said stop peg is free to move from stop to stop;
   (b) lock release access slots;
   (c) said locking means comprising at least one dowel receiving slot, within which said dowel fits without contacting said inner bearing surface, and gradually narrowing limits within which said dowel means is free to move until contacting said inner bearing surface; and
   (d) spring means in said locking means for constant biasing of said dowel means into said gradually narrowing limits so that said dowel means is constantly in contact with said inner bearing surface.

8. The apparatus of claim 7 further comprising:
   (a) a lock release means movably connected to said male half; and
   (b) dowel movement peg means, corresponding in number to said dowel means, attached to said lock release means that protrude through said lock release access slots so that when said lock release means is rotated in one direction said dowel means are forced by said dowel movement peg means into said dowel receiving slot thereby freeing said hinge to move and, when said lock release means is released, said spring means force said dowel means into said narrow limit and in contact with said inner bearing surface.

9. The apparatus of claim 8 further comprising:
   (a) a tensioning means for providing constant tension to move said upper and lower brace members in the free-moving direction;
   (b) said tensioning means comprising a center tension section and two attachment ends;
   (c) one said attachment end attached to said upper brace member and the other attachment end attached to said lower brace member; and
   (d) both said attachment ends reinforced so that stretching and tensioning occurs only in said center tension section.

10. The apparatus of claim 9 further comprising:
    (a) a brake means for braking and preventing movement in said free direction; and
    (b) said brake means comprising a lock nut means and a tightening means so that as said tightening means tightens said lock nut means is drawn into frictional engagement with said outer surface of said female half and movement of said female half is prevented and whereby when said tightening means is untightened said lock nut is released from said frictional engagement and movement of said female half is permitted.

11. A brace and hinge apparatus comprising:
    (a) upper and lower brace members;
    (b) a hinge means comprising a female half attached to the lower brace member or the upper brace member, a male half attached to the opposite brace member, and a dowel means;
    (c) said female half containing an inner bearing surface;
    (d) said male half containing a locking means for locking of dowel means against said inner bearing surface and, thereby, said brace members, in one, locked, direction and allowing unlimited movement in another, free, direction;
    (e) a lock release means for allowing movement in said locked direction;
    (f) a tensioning means for providing constant tension to move said upper and lower brace members in the free-moving direction;
    (g) a brake means for braking and preventing movement in said free direction; and
    (h) a stop means to prevent hyperextension of a joint to which said brace and hinge are attached.

12. A brace and hinge method comprising the steps of:
    (a) constructing upper and lower brace members;
    (b) attaching a hinge means comprising a female half attached to the lower brace member or the upper brace member, a male half attached to the opposite brace member, and a dowel means;

(c) providing an inner bearing surface in said female half; and (d) providing a locking means in said male half that locks said dowel means against said inner bearing surface and, thereby, said brace members when moved in one, locked, direction and that allows unlimited movement in another, free, direction.

13. The method of claim 12 further comprising the step of providing a lock release means for allowing movement in said locked direction.

14. The method of claim 12 further comprising the step of providing a brake means for braking and preventing movement in said free direction.

15. The method of claim 12 further comprising the step of adding a stop means to prevent hyperextension of a joint to which said brace and hinge is attached.

16. The method of claim 12 further comprising the steps of:

(a) providing an outer surface to said female half;

(b) constructing said female half so that said locking means and said dowel means fit within, and are surrounded by, said inner bearing surface; and (c) attaching a stop peg to said female half.

17. The method of claim 16 further comprising the steps of:

(a) constructing, in said male half, an outer race with beginning and ending stops along which said stop peg is free to move from stop to stop;

(b) providing lock release access slots in said male half;

(c) constructing said locking means with at least one dowel means receiving slot, within which said dowel means fits without contacting said inner bearing surface, and with gradually narrowing limits within which said dowel means is free to move until contacting said inner bearing surface; and adding spring means in said locking means for constantly biasing said dowel means into said gradually narrowing limits so that said dowel means is constantly in contact with said inner bearing surface.

18. The method of claim 17 further comprising the steps of:

(a) movably connecting a lock release means to said male half; and (b) attaching dowel movement peg means, corresponding in number to said dowel means, to said lock release means that protrude through said lock release access slots so that rotation of said lock release means in one direction forces said dowel means, by said dowel movement peg means, into said dowel receiving slot thereby freeing said hinge to move and, when said lock release means is released, said spring means force said dowel means into said narrow limit and in contact with said inner bearing means.

19. The method of claim 18 further comprising the steps of:

(a) providing a tension means, with a center tension section and two attachment ends;

(b) attaching one attachment end to said upper brace member and the other attachment end to said lower brace member; and (c) reinforcing said attachment ends so that stretching and tensioning occurs only in said center tension section.

20. The method of claim 19 further comprising the step of providing a brake means with a lock nut means and a tightening means so that as said tightening means tightens said lock nut means is drawn into frictional engagement with said outer surface of said female half and movement of said female half is prevented and whereby when said tightening means is untightened said lock nut is released from said frictional engagement and movement of said female half is permitted.

21. A brace and hinge method comprising the steps of:

(a) constructing upper and lower brace members;

(b) attaching a hinge means comprising a female half attached to the lower brace member or the upper brace member, a male half attached to the opposite brace member, and a dowel means;

(c) providing an inner bearing surface in said female half;

(d) constructing a locking means in said male half that locks said dowel means against said inner bearing surface and, thereby, said brace members when moved in one, locked, direction and that allows unlimited movement in another, free, direction;

(e) adding a lock release means for allowing movement in said locked direction;

(f) providing a brake means for braking and preventing movement in said free direction; and (g) adding a stop means to prevent hyperextension of a joint to which said brace and hinge is attached.

* * * * *

UNITED STATES PATENT AND TRADEMARK OFFICE
CERTIFICATE OF CORRECTION

PATENT NO. : 5,031,606
DATED : July 16, 1991
INVENTOR(S) : Gregg Ring, Sr.

It is certified that error appears in the above-identified patent and that said Letters Patent is hereby corrected as shown below:

In Claim 17, column 9, line 40 of the Patent, add --(d)-- before the word "adding."

In Claim 11, column 8, line 8 of the Patent, insert the word --said-- before "dowel."

Signed and Sealed this

Tenth Day of November, 1992

Attest:

DOUGLAS B. COMER

*Attesting Officer*  *Acting Commissioner of Patents and Trademarks*